(12) United States Patent
McCombs et al.

(10) Patent No.: US 6,427,690 B1
(45) Date of Patent: Aug. 6, 2002

(54) COMBINED OXYGEN REGULATOR AND CONSERVATION DEVICE

(75) Inventors: Norman R. McCombs, Tonawanda; James A. Alessi, Leroy; Michael A. Chimiak, Williamsville; Andrzej Klimaszewski, Lockport, all of NY (US)

(73) Assignee: AirSep Corporation, Buffalo, NY (US)

( * ) Notice: Subject to any disclaimer, the term of this patent is extended or adjusted under 35 U.S.C. 154(b) by 0 days.

(21) Appl. No.: 09/420,826

(22) Filed: Oct. 19, 1999

Related U.S. Application Data

(60) Provisional application No. 60/105,055, filed on Oct. 21, 1998.

(51) Int. Cl.$^7$ ............................................. A61M 16/00
(52) U.S. Cl. ......................... 128/204.26; 128/205.24; 128/224.23
(58) Field of Search ..................... 128/207.18, 204.21, 128/204.26, 205.24, 204.23

(56) References Cited

U.S. PATENT DOCUMENTS

| | | | |
|---|---|---|---|
| 2,766,752 A | 10/1956 | Meidenbaur, Jr. | |
| 4,457,303 A | 7/1984 | Durkan | |
| 4,462,398 A | 7/1984 | Durkan et al. | |
| 4,655,246 A | 4/1987 | Phlipot et al. | |
| 4,823,788 A | * 4/1989 | Smith et al. | 128/205.24 |
| 4,971,049 A | 11/1990 | Rotariu et al. | |
| 5,005,570 A | 4/1991 | Perkins | |
| 5,099,837 A | 3/1992 | Russel, Sr. et al. | |
| 5,165,397 A | * 11/1992 | Arp | 128/204.21 |
| 5,280,780 A | * 1/1994 | Abel | 128/203.14 |
| 5,331,995 A | * 7/1994 | Westfall et al. | 137/8 |
| 5,411,059 A | 5/1995 | Server et al. | |
| 5,440,477 A | 8/1995 | Rohrberg et al. | |
| 5,558,086 A | * 9/1996 | Smith et al. | 128/204.26 |
| 5,697,364 A | * 12/1997 | Chua et al. | 128/204.21 |
| 5,755,224 A | 5/1998 | Good et al. | |
| 5,865,174 A | * 2/1999 | Kloeppel | 128/204.23 |
| 5,881,725 A | * 3/1999 | Hoffman et al. | 128/204.26 |
| 6,152,134 A | * 11/2000 | Webber et al. | 128/205.24 |
| 6,220,244 B1 | * 4/2001 | McLaughlin | 128/204.23 |

OTHER PUBLICATIONS

DeVilbiss Sunrise Medical, "DeVilbiss EX2000D Pulse Dose Conserving Device Instruction Guide", *DHC, Inc.*, pp. 1–18 (1997). (11 pgs).

DeVilbiss Sunrise Medical, "The Hideaway & Walkabout. Patented Pulse Dose Technology in Flexible Lightweight Packages", *DHC, Inc.*, p. 1, (1994). (1 pg).

Peter L. Bliss, et al., "A Bench Study Comparison of Demand Oxygen Delivery Systems and Continuous Flow Oxygen", Respiratory Care, vol. 44, No. 88, pp. 925–931, (Aug. 1999). (7 pgs).

AirSep Corporation, "ImPulse—OCD System Patient Manual", Printed in U.S.A., DPS MN040–1, pp. 1–26, (Apr. 1997). (16 pgs).

* cited by examiner

*Primary Examiner*—Aaron J. Lewis
*Assistant Examiner*—Mital Patel
(74) *Attorney, Agent, or Firm*—Jaeckle Fleischmann & Mugel, LLP

(57) ABSTRACT

A combination flow regulator and conservation device, for oxygen gas or oxygen concentrated gas, attachable to an oxygen tank or wall outlet of a master oxygen system and containing a gas regulator and a control circuit to control both the effective rate and timing of the flow of gas through the device, the control circuit selectively controlling the device to supply the gas to a user in one of at least three selectable modes of operation, the modes including (1) a continuous flow of gas, (2) an intermittent pulse of gas to be supplied on every inhalation stage of the breathing cycle of the user for a variable period of time during the inhalation stage, and (3) an intermittent pulse of gas to be supplied only during selectable inhalation stages of the breathing cycles of the user.

14 Claims, 10 Drawing Sheets

COMBINED OXYGEN REGULATOR AND CONSERVATION DEVICE

This application claims the benefit of U.S. Provisional Application Ser. No. 60/105,055, filed Oct. 21, 1998.

This invention relates to oxygen delivery systems and more particularly to a device for regulating the flow of oxygen from a supply source to a user.

BACKGROUND OF INVENTION

It is well known to use gas flow regulators in conjunction with supply sources of gases such as tanks of oxygen containing high pressure oxygen or oxygen gas mixtures, to control both the pressure and the rate of flow of the oxygen or oxygen mixture being released from the tank. More recently, there have been developed separate oxygen control devices that conserve the oxygen supply by limiting its release only during useful times, as for example, only during the inhalation period of the breathing cycle of a patient using the oxygen. Such devices are sensitive to drops in pressure caused by inhalation to activate the oxygen flow only during inhalation. To control the "effective" rate flow of the oxygen, but without adjusting the regulator, the oxygen in such devices may be supplied at one flow rate but a breath cycle counter employed to selectively activate the flow only at intermittent breathing cycles, for example after each second, third or fourth cycle.

It also is known that only the air or oxygen inhaled at the initial or effective stage of inhalation or inspiration, is that which is usefully absorbed by the lungs. The remaining inhaled air or oxygen in the latter stage of inhalation is usually exhaled before it can be absorbed by the lungs. To take advantage of this phenomenon, there are devices that conserve oxygen supplies even more by actuating the flow of gas upon initial inhalation but also terminating the flow of oxygen after the effective stage, say 190 ms after initial inhalation. With such devices, it is known to increase or decrease the effective flow rate of the oxygen by increasing or decreasing the activation time during each inhalation cycle.

As all of the above features are either necessary or desirable and useful, we have invented a new combined oxygen regulator and conservation device that is flexible in its use, compact in size, simple and convenient to set and operate in its modes of operation, and further can increase the mobility of users of the oxygen supply.

SUMMARY OF THE INVENTION

The present invention comprises a combination regulator and conservation device that conveniently can be positioned directly on an oxygen tank containing oxygen or an oxygen mixture in gas or liquid form, or the wall outlet of a master oxygen system, for connection directly to the tank or outlet, thereby eliminating the need for a separate hose between the regulator and the conservation device. Contained within the device in a compact package is an oxygen regulator, a power supply or external power supply connection, and a control circuit to control the effective dose of oxygen by control of the interval(s) and time(s) of the oxygen flow. Further according to our invention, the device can be selectively controlled to provide either an intermittent pulse of oxygen to be supplied on every inhalation stage cycle at variable times during the inhalation stage, or an intermittent oxygen supply mode delivering a predetermined amount of oxygen but only during selectable alternating inhalation cycles, or an override mode for a continuous supply of oxygen.

BRIEF DESCRIPTION OF THE DRAWINGS

The invention as well as its features and advantages will become more apparent from the following description of a preferred embodiment of the invention and the accompanying drawings in which like numerals represent like parts.

DETAILED DESCRIPTION OF THE PREFERRED EMBODIMENT

Figure 1:
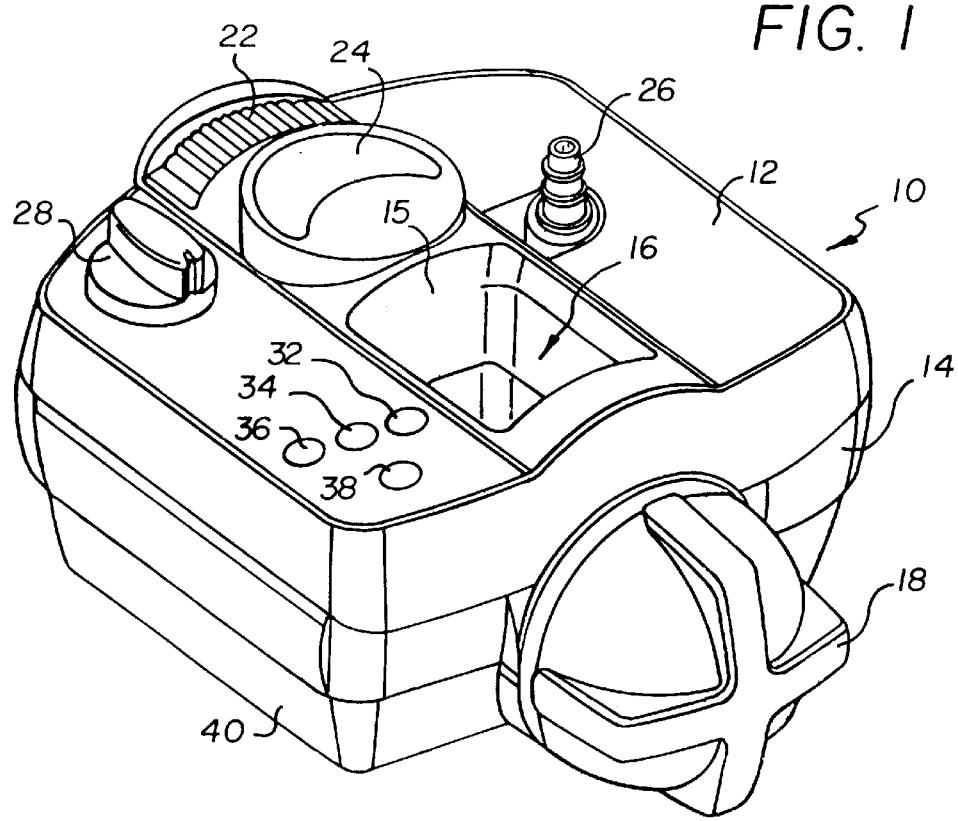
FIG. 1 is a perspective view of a combination oxygen regulator and conservation device according to the invention, as viewed from the front and top of the device.
Figure 2:
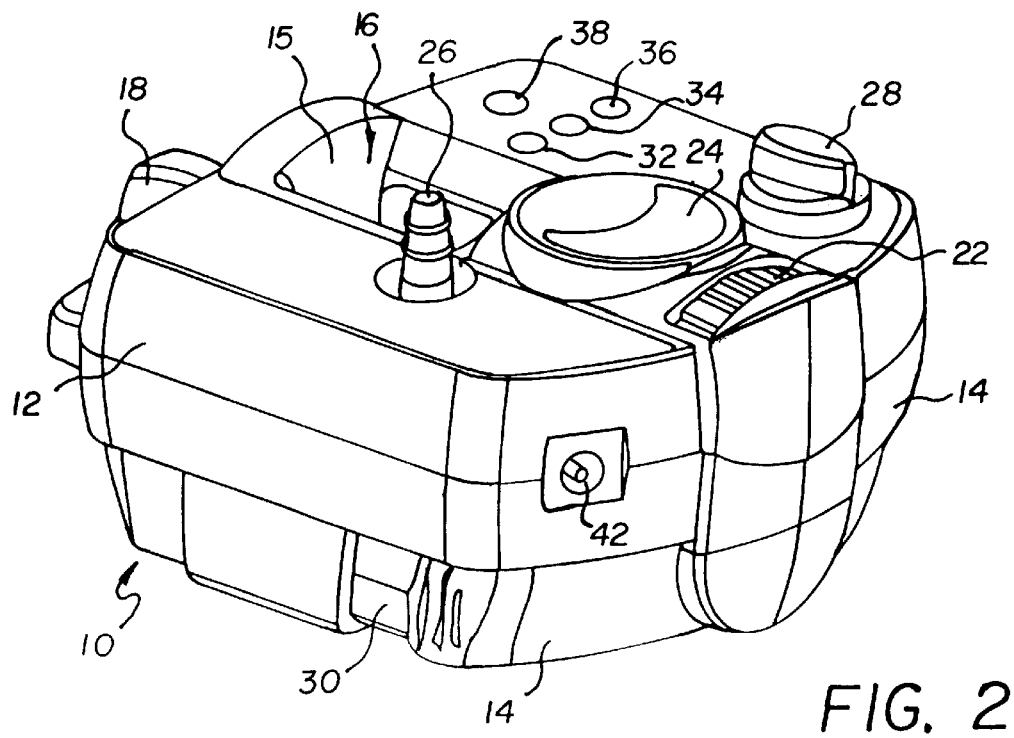
FIG. 2 is another perspective view device of FIG. 1, as viewed from the back and top of the device.

As shown in FIGS. 1 and 2, the external components of the device 10 according to our invention include a top housing component 12 and a bottom housing component 14. When assembled, the inner walls 15 of the housing components 12, 14 define a central pass-through aperture 16, into which may be inserted the neck of an oxygen tank (not shown) or the valve connector of an oxygen wall outlet (not shown) by the use of known alignment pins 17. At the front of device 10 is a rotatable knob 18 to hold device 10 in operating position on the oxygen tank valve or wall outlet, at which position the tank valve or wall outlet may be opened to permit oxygen to flow through a flow regulator 20 located between the housing components 12, 14. As further shown in FIGS. 1 and 2, device 10 includes an accessible on/off switch 22, an oxygen flow gauge 24 to measure the remaining supply of oxygen in the supply tank, and an outlet fitting 26 connectable to the user of the oxygen by a cannula tube or the like (not shown). To vary the "effective" rate of oxygen flowing through device 10 to the user, there is provided a rotatable selector switch 28 to permit a change in the flow time and/or frequency of oxygen operation of device 10 in either one of at least two intermittent oxygen supply modes, as well as a mechanical bypass valve 30 to override the selected intermittent mode to cause a continuous flow of oxygen. Among the remaining visible elements are a number of LED visual indicators 32, 34, 36 indicators, a battery test button 38, a battery compartment door 40 and an external power supply connector 42.

Figure 3:
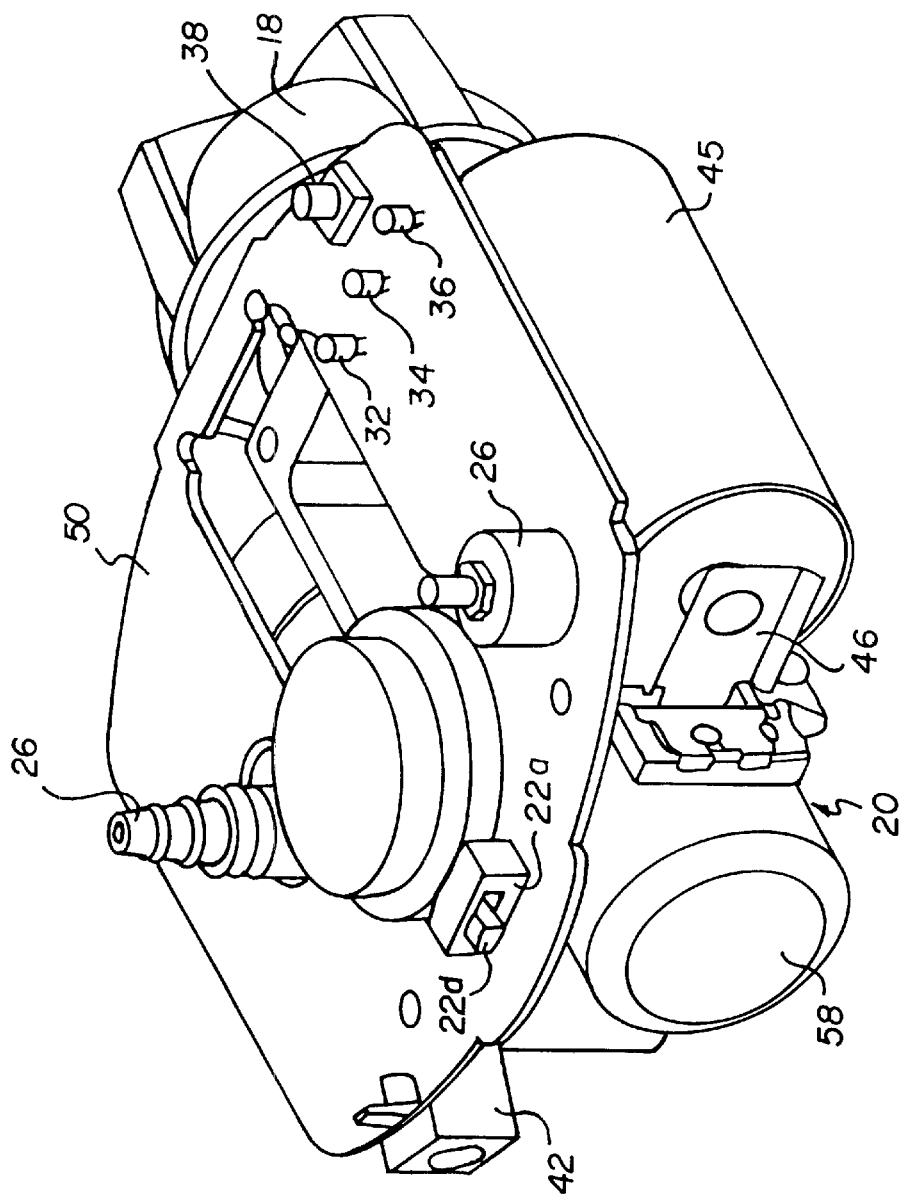
FIG. 3 is a perspective view of the device of FIG. 1, but with the covers removed to illustrate the internal components.
Figure 4:
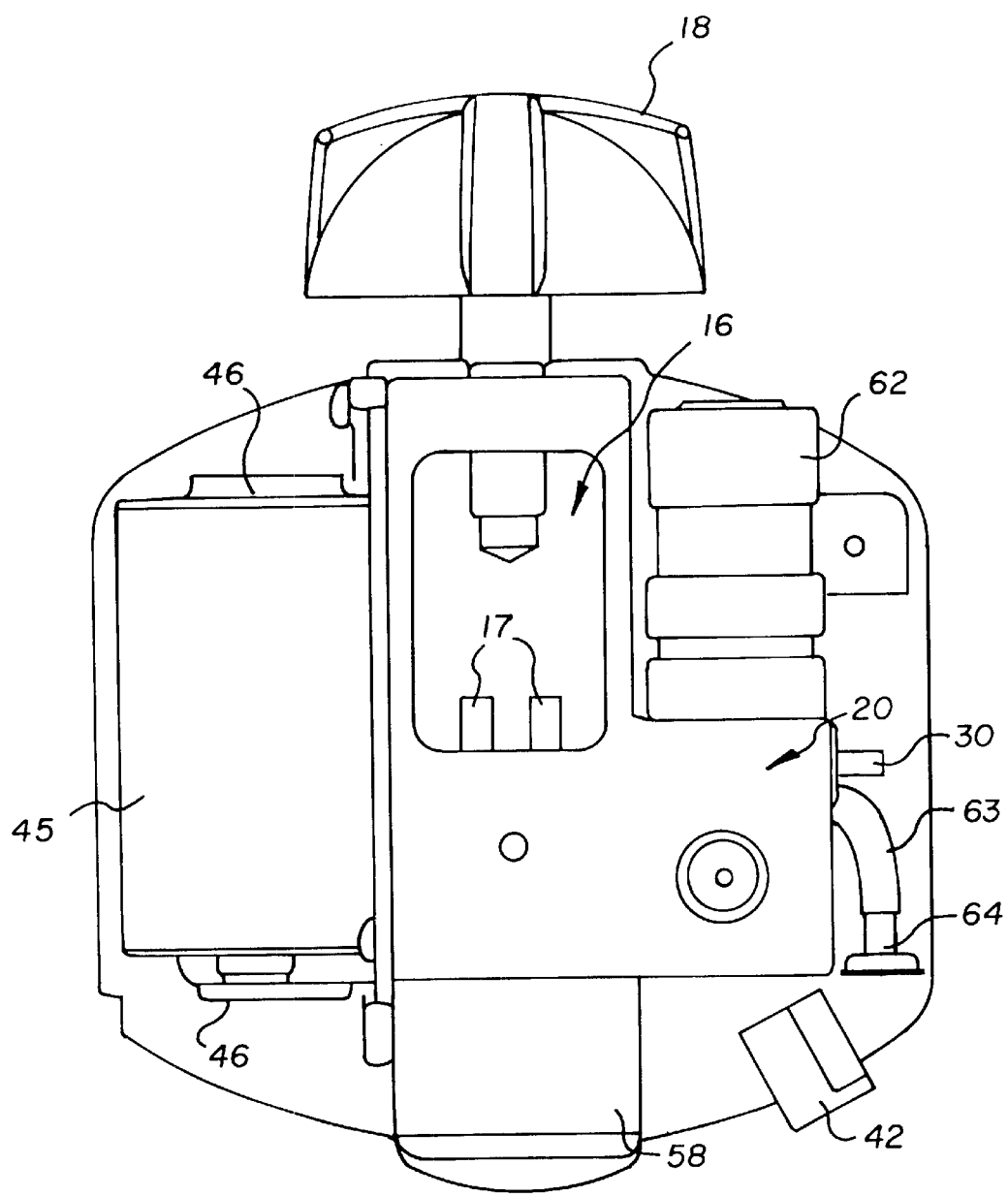
FIG. 4 is a bottom view of the device with the covers removed.
Figure 5A:
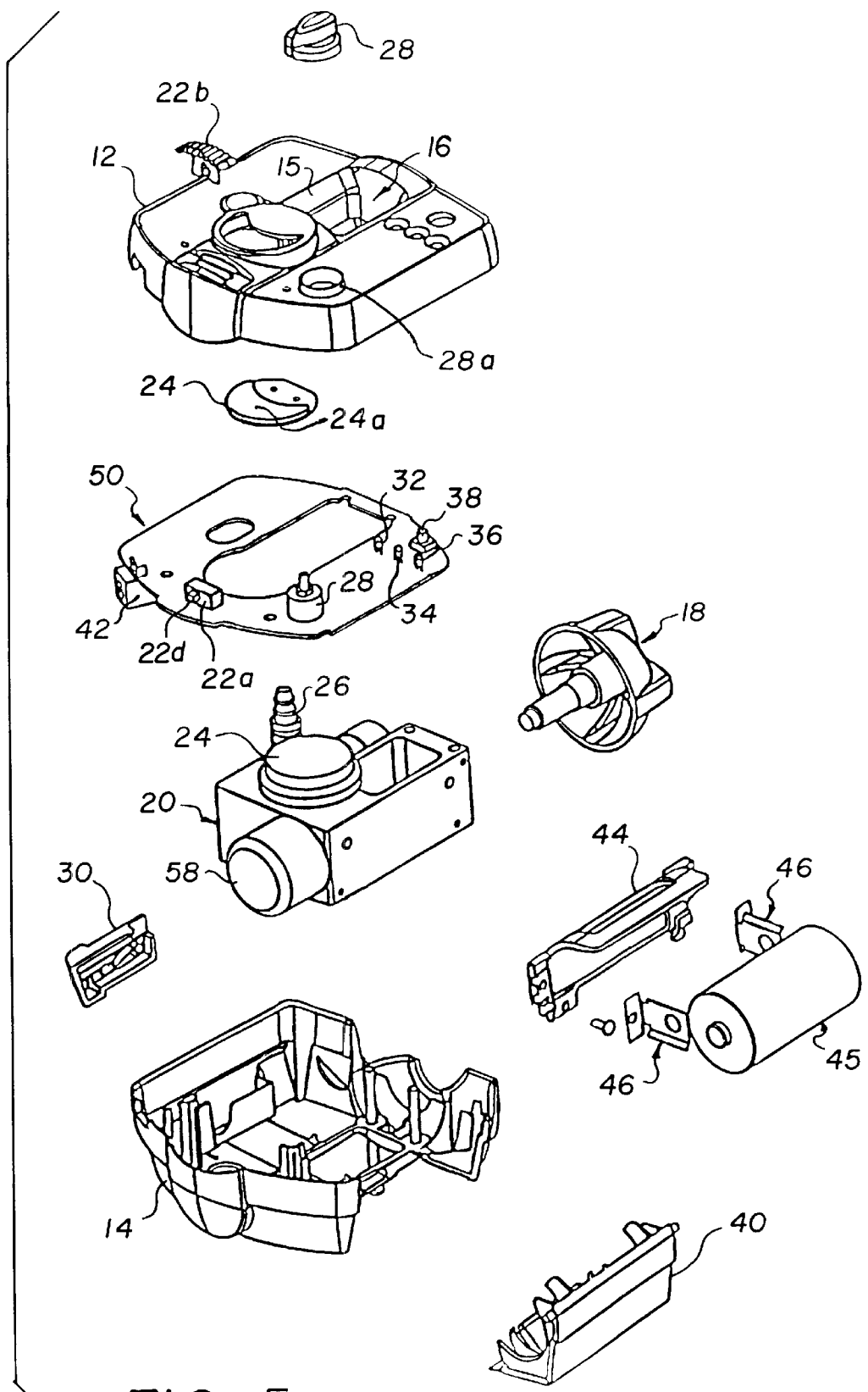
FIG. 5*a* is an exploded view of various components of the preferred embodiment of the invention.
Figure 5B:
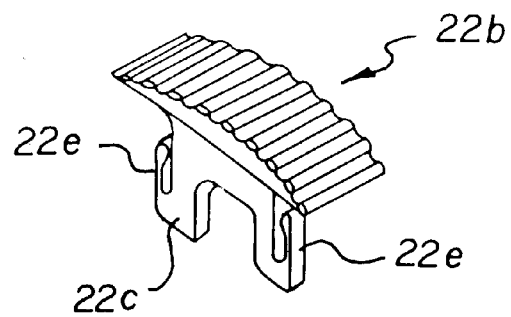
FIG. 5*b* is an enlargement of the accessible part of the device's on-off button.

Referring now to FIGS. 3 through 5, the operating elements of the device include the oxygen flow regulator 20 mounted in the bottom housing component 14. Formed by and within the housing components 12, 14 is a battery compartment 44 containing the battery 45, battery connectors 46 and a mode control switch 48 to be described. Mounted above regulator 20 is a circuit board 50 supporting an electronic circuit 52 which contains the various switches and flow control circuit components to be described, along with the wiring and leads necessary to complete circuit 52. Further supported by regulator 20 is flow gauge 24.

To effectively seal the internal components of device 10 from spilled liquids and the like, top housing component 12 includes raised surfaces below selected ones of the external parts, such as rotatable selector switch 28, as shown at 28a, as well as a transparent cover for gauge 24, as shown at 24a, and an O-ring, not shown, to seal the cover at outlet 26.

In addition and as shown by FIGS. 5 and 5a, we have provided means housing component 12, without requiring the detachment of any electrical leads, by mounting the operating portion 22a of on-off switch 22 on circuit board 50, and a further accessible slide button 22b having slotted arm 22c defining a slot with bottom beveled edges and extending through top cover component 12 to engage and position the slidable contact 22d within the slot. Arm 22c of button 22b further includes a pair of spring arms 22e to detachably hold button 22b on top cover component 12.

Figure 6A:
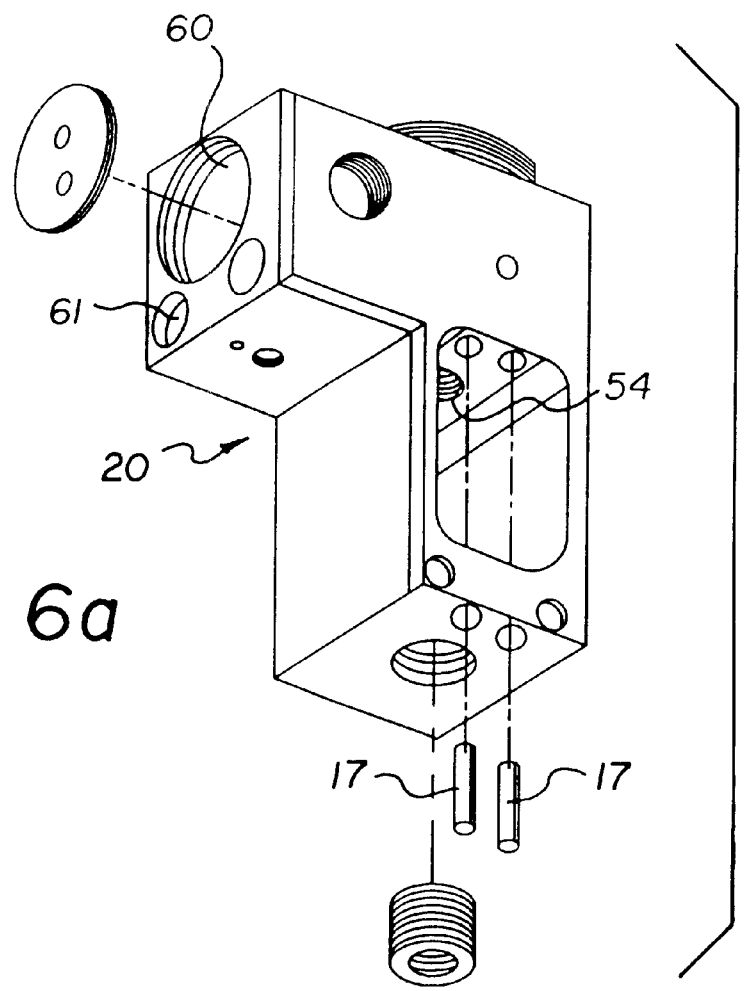
FIGS. 6*a* through 6*c* are views of certain elements of the oxygen regulator component of the invention.
Figure 6B:
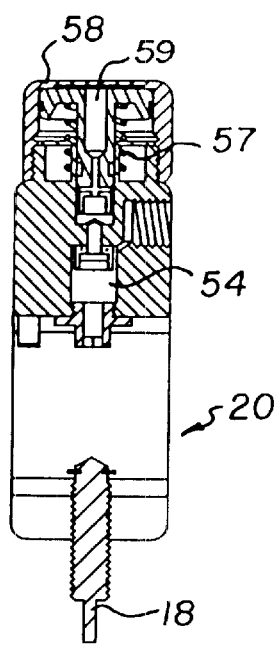
Figure 6C:
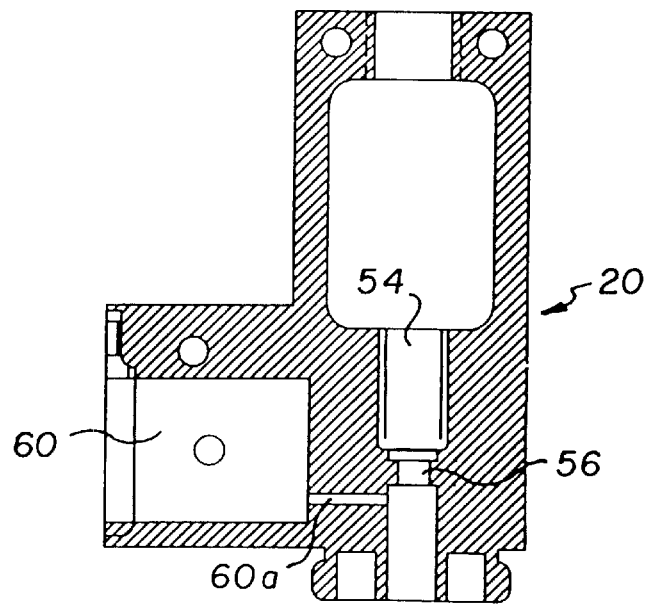
Figure 7:
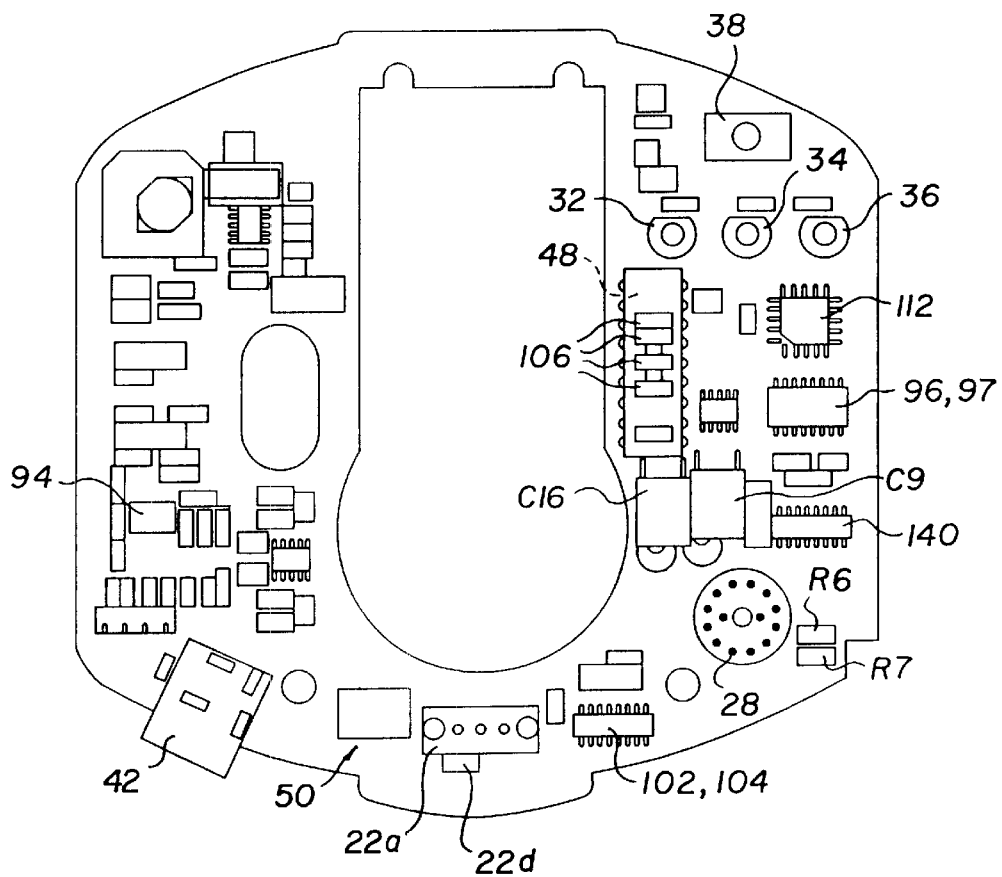
FIGS. 7, 8, 9 and 10 are top, bottom, side and end views, respectively, of the control circuit component containing the electronic circuit elements of the invention.
Figure 8:
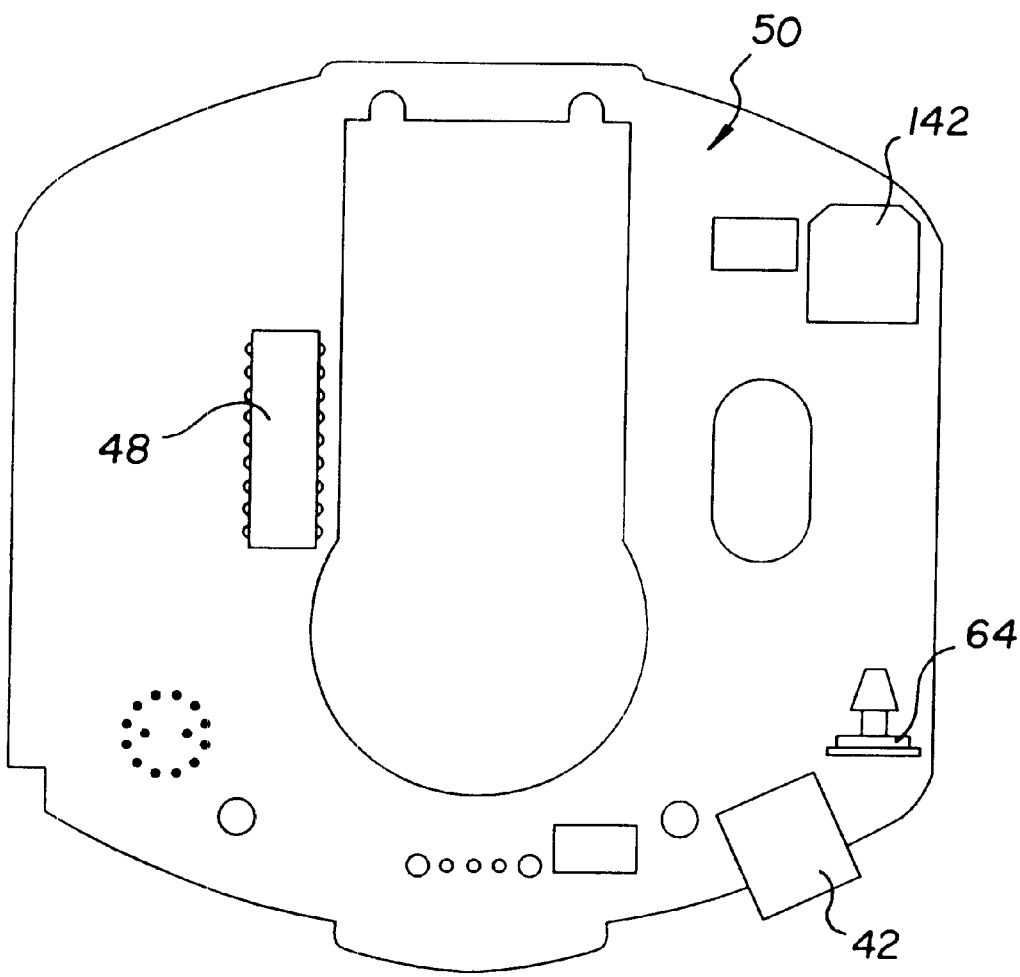
Figure 9:
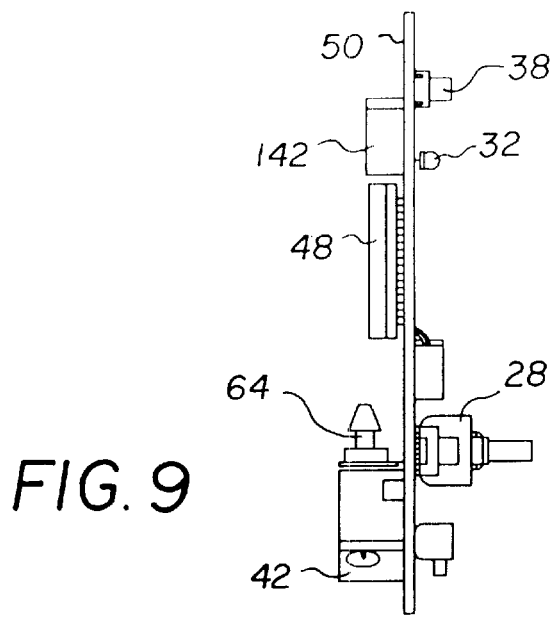
Figure 10:
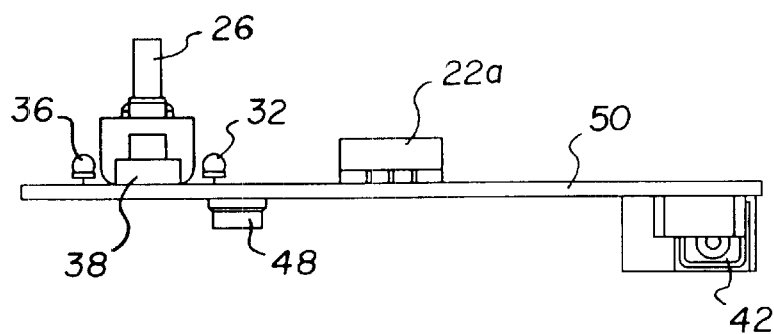

As seen in FIGS. 6a through 6c, the oxygen flow regulator 20, the flow regulation of which in operation is similar in principle to known regulators, includes a fluid connection 54 between the oxygen tank valve and a first chamber 56 of the regulator 20, which controls the pressure of the supplied oxygen by a regulator spring 57 and piston 59 contained in a cap 58 attached to the regulator 20 as shown. Chamber 56 also provides a fluid port to flow gauge 24 to indicate the amount of oxygen in the tank as approximated by its pressure. According to our invention, we have provided a second or oxygen volume chamber 60 in regulator 20 and in fluid connection with chamber 56 by a port connecting the chambers 56 and 60. Chamber 60 maintains a predefined volume of oxygen at a pre-set pressure, and from which the oxygen flow to the user is controlled by either a solenoid valve 62 in a pulse mode through one port in chamber 60, the timing of which valve is activated by the control circuit 52 according to the invention, or by the mechanical bypass valve 30 connected to another port in chamber 60 to operate in the continuous mode.

The second chamber 60 of regulator 20 includes yet another port 61 in fluid connection by suitable tubing 63 both with outlet 26 and with a pressure sensing transducer 64 on the circuit board, in order to activate the solenoid operated valve 62 in response to a pressure reduction at outlet 26 and port 61, as caused by inhalation from the user.

Figure 11:
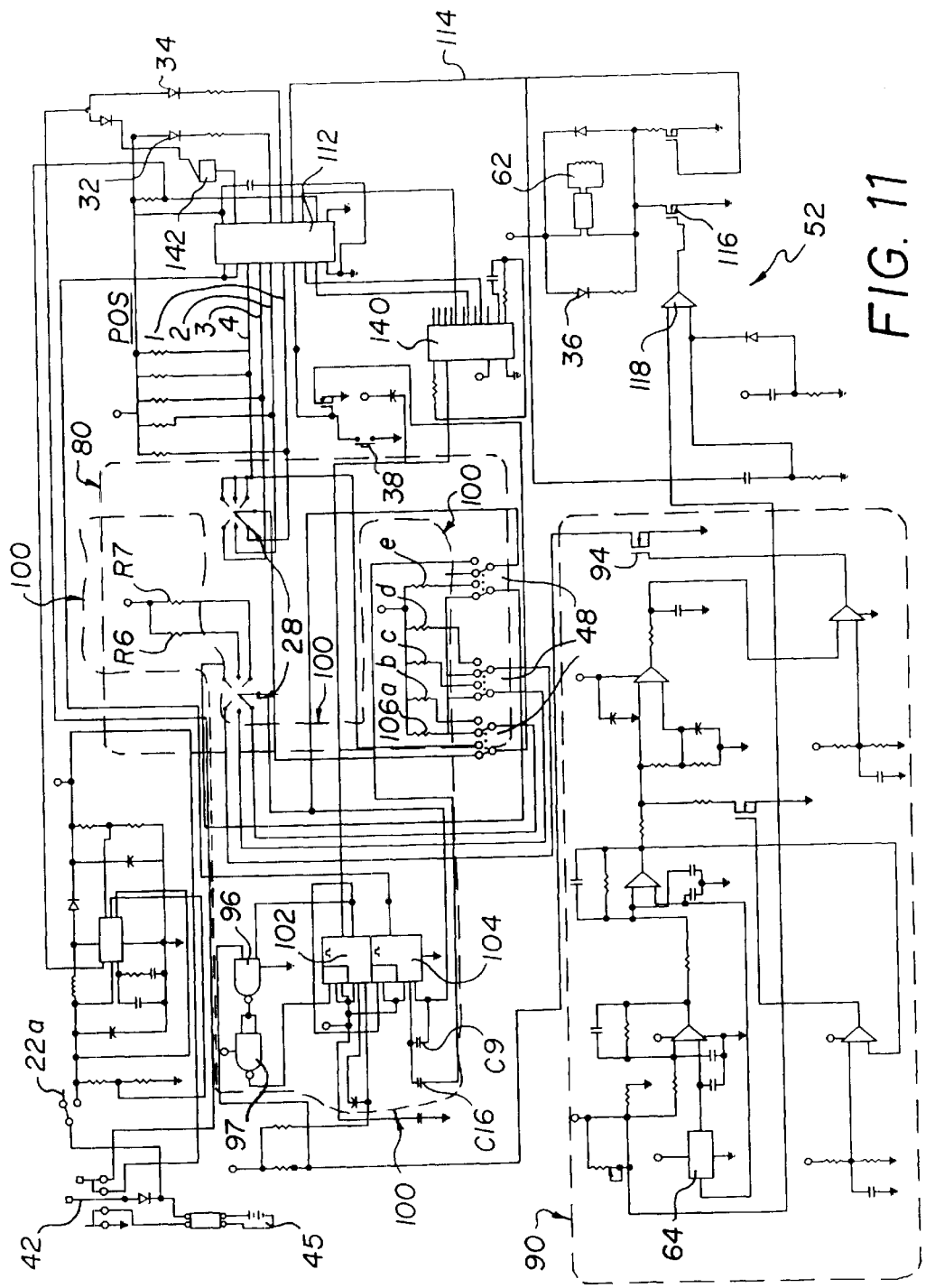
FIG. 11 is a diagram of the circuit of the preferred embodiment that enables the combined features and selective modes of operation.

Referring now to FIGS. 7 through 10, mounted on circuit board 50 are the enclosed portion 22a of on/off slide switch 22 to activate the circuit 52, and the slidable mode control switch 48 to one of two intermittent operating mode options as will be described. Also mounted on circuit board 50 are the three LED indicators 32, 34 and 36 and battery test button 38. The remaining elements of the circuit 52 will be better understood by reference to the circuit diagram of FIG. 11.

As shown in FIG. 1, power is supplied to circuit 52 either by battery 45 or an external power supply (not shown) attached to connector 42. The circuit elements generally comprise a control selection subcircuit 80 containing the slidable mode control switch 48 and the rotatable selector switch 28. For purposes of illustration in circuit 52, slide switch 48 (which comprises a double pole, six throw switch) is shown as being set in the A mode (intermittent fixed time flow during alternate breath cycles) but can be set in its B mode (variable time pulses during inhalation in all breath cycles). The rotary selector switch 28 (a double pole, six throw switch) sets the timing of pulses in the two operating modes A and B.

In modes A and B, a breath response subcircuit 90 of circuit 52 activates the flow of oxygen in response to a reduced air pressure as sensed by the pressure sensing transducer 64, the voltage from which is amplified and compared to a reference, preset voltage, such that when the reference voltage level is reached, transistor 94 is turned on to close logic gates 96 and 97. A third pulse timing subcircuit 100 of circuit 52 determines the timing of oxygen flow by generating a predetermined pulse and includes a pair of one-shot devices 102 and 104, which are enabled when gates 96 and 97 are closed, that provide current to create an electrical pulse for a predetermined period of time. As a safety feature, one-shot device 102 acts as a delay, say for 720 ms, to prevent a second activation within that time period as might be caused by hyperventilation of the user. To control the pulse time, there are provided a number of resistors (106a through 106c, R6 and R7) and capacitors C9 and C16 connected as shown. In mode A, resistor 106a and capacitor C9 control a common pulse time for positions 1 through 4 of switch 28, and in combination with resistors R6 and R7 for positions 5 and 6 respectively, of selector switch 28 for increased pulse times about 25% and 50% greater, respectively. Alternatively, for mode B, capacitors C9 and C16 together with resistors 106b (position 1 of switch 28), 106c (position 2), 106d (position 3) and 106e (position 4), as well as resistor 106e together with resistors R6 and R7 for positions 5 and 6, respectively and vary the operational times when selector switch 48 is set for mode B in combination with positions 1 through 6 of selector switch 28. The generated predetermined pulse is then transmitted to a programmable array logic (PAL) chip 112 which in turn transmits the pulse as an output of the predetermined length during inhalation, but only in the appropriate breath cycles for mode A (every fourth breath for position 1, every other breath for position 2, three of four breaths for position 3 and every breath for positions 4, 5 and 6), and in all breath cycles for mode B. When PAL chip 112 produces the appropriate output signal supplied through line 114, it activates solenoid valve 62 for the selected operational time to close the circuit to solenoid valve 62 and permit the oxygen to flow from chamber 60 through the outlet 26. The logic of the operation in both modes A and B is contained within PAL chip 112 and, based on the appropriate input, marked as POS 1 through POS 4, based on the setting of selector switch 28 and in which POS 4 provides the input for each of switch 28 positions 4, 5 and 6, the output signal from the chip 112 either will permit or will not permit the intermittent pulses of oxygen to flow to outlet 26, to approximate example, one, two, three, four, five and six liters per minute "effective" flow rate, respectively, for the six positions of switch 28.

To conserve battery life, an extra timing switch 116 from a comparator 118 is closed only for the initial 20 ms after initial activation of transducer 64 to overcome the static inertia (and any valve "seal") of solenoid valve 62, which after activation valve 62 can be maintained by the control line 114.

Figure 12:
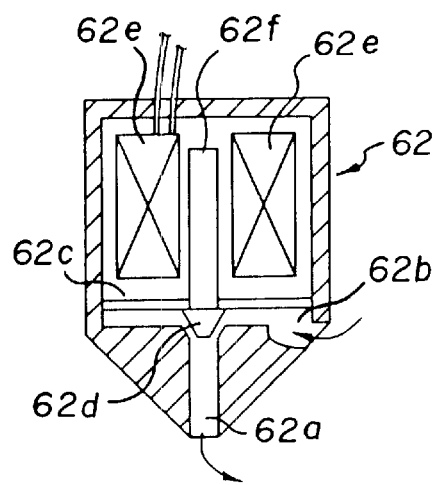
FIG. 12 is a cross sectional view of the solenoid valve used with the invention.

We have also discovered that we can further conserve the battery by reversing the direction of flow of oxygen through the solenoid valve 62, as shown by FIG. 12. In the prior art, oxygen under pressure from the supply normally enters valve 62 by its center port 62a and exits through a peripheral port 62b at atmospheric pressure. A "spider" spring 62c is used to hold the valve seat 62d in position to close port 62a. Valve coil 62e creates a magnetic field to move armature 62f to overcome spring 62c and open valve seat 62d. However, by reversing the direction of flow to provide for the pressurized oxygen to flow into port 62b, the higher fluid pressure from the oxygen supply chamber 60 now works together with, rather than against, spring 62c, the result being that a lower spring strength is required and therefore less electrical power (by as much as about 50%) needed for the solenoid coil 62e to overcome the force of spring 62c.

Completing the circuit are LED 36 to indicate the pulse flow, LED 34 to indicate a low battery condition if the battery test button 38 is depressed, and LED 32 which functions as a visual alarm for the following purpose. As a further safety device, there is provided a time counter 140 which is restarted at every breath cycle and set to cycle through, e.g., 30 seconds. If another breath is detected before the 30 second cycle, the counter is again zeroed out and restarted, but if no breath is detected, then an alarm is generated, which may comprise either or both a visual alarm, in this case LED 32, and an audible alarm as indicated by internal buzzer 142. As shown in circuit 52, audible alarm 142 may also be disabled when device 10 is connected to an external power source, as for example in situations such as a hospital setting where an audible alarm may be inappropriate.

As is evident from the invention as disclosed, this specification, an alternative embodiment of the invention is to add at least one further mode of operation, namely to supply oxygen throughout substantially the entire inhalation stage of every breathing cycle and/or selected breathing cycles, during which oxygen is to be inhaled, by adding a further position to mode selector switch 48, either to connect a set of alternate timing resistors in conjunction with operation of selector switch 28 in mode A or B, or to provide a signal to PAL chip 112 to terminate the output signal of PAL chip 112 in response to an increase in pressure as sensed by the pressure sensing transducer 64 when the user starts to exhale.

In operation, the desired mode of operation is determined by positioning the mode control switch 48 in the battery compartment to either its A or B operating mode position and a battery inserted. With the battery door closed and the on/off switch 22 in its off position, device 10 is then placed in its operating position over the neck of an oxygen tank or wall outlet of an oxygen supply system using alignment pins 17 and regulator knob 18 turned to hold device 10 in position to provide the fluid connection of the oxygen supply tank valve with first chamber 56 of regulator 20. The valve on the oxygen supply tank is then opened. In the normal intermittent operating mode A or B, the continuous flow override valve 30 is closed, and the rotatable selector switch 28 is rotated to one of its six operating positions to indicate the equivalent flow rate of the supplied oxygen, e.g., from 1 through 6 liters per minute. An oxygen delivery device, such a nose cannula, is then attached by its connecting tube to outlet fitting 26, and device 10 turned on by its on/off switch 22 after the patient attaches the nose cannula to his nose.

If mode selector switch 48 is set in its mode A, then the oxygen is supplied for the fixed times at the alternating breaths described. If mode selector switch 48 is set in the B mode, then circuit 52 as described above will activate the oxygen supply during the initial, effective inhalation stages at the varied times described. The various settings and the effective flow rates as controlled by circuit 52 are indicated in the following Table 1, which illustrates the described two modes A and B of intermittent operation and the respective preferred pulse times and doses of oxygen for each of the settings of switch 28 for each mode as selected by switch 28:

TABLE 1

| Mode Select Switch (48) | Rotary Switch (28) Setting | Pulse Frequency Per Four Breath Cycles | Pulse Time (ms) Each Breath Cycle | Oxygen Dose (ml) Each Breath Cycle | Total Dosage (ml) Per Four Breath Cycles |
|---|---|---|---|---|---|
| A | 1 | 1/4 | 184 | 35.0 | 35 |
| A | 2 | 2/4 | 184 | 35.0 | 70 |
| A | 3 | 3/4 | 184 | 35.0 | 105 |
| A | 4 | 4/4 | 184 | 35.0 | 140 |
| A | 5 | 4/4 | 232 | 44.0 | 176 |
| A | 6 | 4/4 | 277 | 52.0 | 208 |
| B | 1 | 4/4 | 93 | 16.5 | 66 |
| B | 2 | 4/4 | 175 | 33.0 | 132 |
| B | 3 | 4/4 | 261 | 49.5 | 198 |
| B | 4 | 4/4 | 348 | 66.0 | 264 |
| B | 5 | 4/4 | 438 | 82.5 | 330 |
| B | 6 | 4/4 | 530 | 99.0 | 396 |

If the user is unsatisfied with the amount of oxygen provided by device 10 in the pre-set intermittent mode A or B, the user may then override the set mode A or B by opening the continuous flow valve 30 to bypass the fluid connection controlled by solenoid valve 62 and thus provide oxygen continuously throughout inhalation and exhalation in all breathing cycles. The mode selector switch 48 as shown preferably is made less accessible to the user, because the appropriate mode of oxygen supply may better be determined by the professional prescribing the device. If no breath cycles are sensed for 30 seconds, the alarm buzzer 142 and LED 32 are activated, whereas the pressure gauge 24 determines when the amount of oxygen in the tank is below a predetermined amount, as for example an amount to produce less than a 500 psig pressure, to indicate the need to replace the tank.

Thus, it can seen that the invention as described contains a number of advantageous features and selectable modes in a compact device that reduces the number of connections and increases the potential of patient mobility. For example, the number of operating modes and the pulse times and frequency of settings may be varied or increased by using the principle disclosed herein. It is further understood that various modifications and substitutions may be made to the described embodiment without departing the spirit and scope of the invention as claimed.

We claim:

1. A combination flow regulator and conservation device for supplying oxygen gas or oxygen concentrated gas to a user during the breathing cycles of the user, the device comprising means for regulating flow of the gas through the device, means for attaching the device to a tank containing or an outlet of a system supplying the oxygen or oxygen concentrated gas, and means for controlling both an effective rate and timing of the flow of gas through the device to selectively supply the gas to the user in one of at least three selectable modes of operation, the modes of operation including (a) first means for supplying a continuous flow of gas through at least the inhalation cycles of the user, (b) second means for providing an intermittent pulse of gas supplied to the user on at least the initial stage of inhalation of substantially every breathing cycle of the user, the second means including means for supplying the pulse of gas at selectively different periods of time during the initial stage of inhalation, and (c) third means for supplying an intermittent pulse of gas to the user at selectively different effective rates of flow of the gas, the pulse supplied by the third means being of a fixed time period for at least two of the selective effective rates, and the effective rates of the third means being determined by supplying the gas at selectable inhalation stages of the breathing cycles of the user.

2. A combination flow regulator and conservation device according to claim 1, and further comprising means for sensing an absence of inhalation by the user after a predetermined time and for activating an alarm if no inhalation is sensed during that predetermined time.

3. A combination flow regulator and conservation device according to claim 2, and further comprising means for selectively activating and deactivating the alarm.

4. A combination flow regulator and conservation device for supplying oxygen gas or oxygen concentrated gas to a user during the breathing cycles of the user, the device comprising means for regulating flow of the gas through the device, means for attaching the device to a tank containing or an outlet of a system supplying the oxygen or oxygen concentrated gas, and means for controlling both an effective rate and timing of the flow of gas through the device to selectively supply the gas to the user in one of at least three selectable modes of operation, the modes of operation including (a) first means for supplying a continuous flow of gas through at least the inhalation cycles of the user, (b) second means for providing an intermittent pulse of gas supplied to the user on at least the initial stage of inhalation of substantially every breathing cycle of the user, the second means including means for supplying the pulse of gas at selectively different periods of time during the initial stage of inhalation, and (c) third means for supplying an intermittent pulse of gas to the user at selectively different effective rates of flow of the gas, the pulse supplied by the third means being of a fixed time period for at least two of the selective effective rates, and the effective rates of the third means being determined by supplying the gas at selectable inhalation stages of the breathing cycles of the user, wherein the means for regulating the flow of the gas includes means defining a first chamber for controlling the pressure of the gas and means defining a second chamber in fluid connection with the first chamber for maintaining a predetermined amount of gas at the controlled pressure, and wherein the means for controlling both the effective rate and the timing of the flow of gas further comprises valve means for discharging the gas maintained in the second chamber, and means responsive to an inhalation by the user for actuating the valve means.

5. A combination flow regulator and conservation device for supplying oxygen gas or oxygen concentrated gas to a user during the breathing cycles of the user, the device comprising means for regulating flow of the gas through the device, means for attaching the device to a tank containing or an outlet of a system supplying the oxygen or oxygen concentrated gas, and means for controlling both an effective rate and timing of the flow of gas through the device to selectively supply the gas to the user in one of at least three selectable modes of operation, the modes of operation including (a) first means for supplying a continuous flow of gas through at least the inhalation cycles of the user, (b) second means for providing an intermittent pulse of gas supplied to the user on at least the initial stage of inhalation of substantially every breathing cycle of the user, the second means including means for supplying the pulse of gas at selectively different periods of time during the initial stage of inhalation, and (c) third means for supplying an intermittent pulse of gas to the user at selectively different effective rates of flow of the gas, the pulse supplied by the third means being of a fixed time period for at least two of the selective effective rates, and the effective rates of the third means being determined by supplying the gas at selectable inhalation stages of the breathing cycles of the user, and further comprising a removable cover portion to enclose at least part of the controlling means, and a switch to alternately activate and deactivate at least a portion of the control means, the switch comprising a first enclosed element connected to the control means and movable to activate and deactivate the portion of the control means and a second accessible element detachably connectable to the enclosed element through the cover portion to cause movement of the enclosed element but releasable from the enclosed element on removal of the cover portion.

6. A combination flow regulator and conservation device for supplying oxygen gas or oxygen concentrated gas to a user during the breathing cycles of the user, the device comprising means for regulating flow of the gas through the device, means for attaching the device to a tank containing or an outlet of a system supplying the oxygen or oxygen concentrated gas, and means for controlling both an effective rate and timing of the flow of gas through the device to selectively supply the gas to the user in one of at least four selectable modes of operation, the modes of operation including (a) first means for supplying a continuous flow of gas through at least the inhalation cycles of the user, (b) second means for providing an intermittent pulse of gas supplied to the user on at least the initial stage of inhalation of substantially every breathing cycle of the user, the second means including means for supplying the pulse of gas at selectively different periods of time during the initial stage of inhalation, (c) third means for supplying an intermittent pulse of gas to the user at selectively different effective rates of flow of the gas, the pulse supplied by the third means being of a fixed time period for at least two of the selective effective rates, and the effective rates of the third means being determined by supplying the gas at selectable inhalation stages of the breathing cycles of the user, and (d) fourth means for providing an intermittent pulse of gas supplied to the user substantially throughout the stage of inhalation, means responsive to initiation of inspiration by the user for initiating the pulse of gas, and means responsive to the start of exhalation by the user for terminating the flow of gas to the user.

7. A combination flow regulator and conservation device according to claim 6, wherein the fourth means supplies the gas during inspiration of every breathing cycle of the user.

8. A combination flow regulator and conservation device according to claim 6, wherein the fourth means further comprises selector means for supplying the gas during inspiration of selected breathing cycles of the user.

9. A combination flow regulator and conservation device for supplying oxygen gas or oxygen concentrated gas to a user during the breathing cycles of the user, the device comprising means for regulating flow of the gas through the device, means for attaching the device to a tank containing or an outlet of a system supplying the oxygen or oxygen concentrated gas, and means for controlling both an effective rate and timing of the flow of gas through the device to selectively supply the gas to the user in one of at least three selectable modes of operation, the modes of operation including (a) first means for supplying a continuous flow of gas through at least the inhalation cycles of the user, (b) second means for providing an intermittent pulse of gas supplied to the user on at least the initial stage of inhalation of substantially every breathing cycle of the user, the second means including means for supplying the pulse of gas at selectively different periods of time during the initial stage of inhalation, and (c) third means for supplying an intermittent pulse of gas to the user at selectively different effective rates of flow of the gas, the pulse supplied by the third means being of a fixed time period for at least two of the selective effective rates, and the effective rates of the third means being determined by supplying the gas at selectable inhalation stages of the breathing cycles of the user, wherein the third means includes means for selectively increasing the fixed time period in at least one of the selective effective rates.

10. A combination flow regulator and conservation device for supplying oxygen gas or oxygen concentrated gas to a user during the breathing cycles of the user, the device comprising means for regulating flow of the gas through the device, means for attaching the device to a tank containing or an outlet of a system supplying the oxygen or oxygen concentrated gas, and means for controlling both an effective rate and timing of the flow of gas through the device to selectively supply the gas to the user in one of at least three selectable modes of operation, the modes of operation including (a) first means for supplying a continuous flow of gas through at least the inhalation cycles of the user, (b) second means for providing an intermittent pulse of gas supplied to the user on at least the initial stage of inhalation of substantially every breathing cycle of the user, the second means including means for supplying the pulse of gas at selectively different periods of time during the initial stage of inhalation, and (c) third means for supplying an intermittent pulse of gas to the user at selectively different effective rates of flow of the gas, the pulse supplied by the third means being of a fixed time period for at least two of the selective effective rates, and the effective rates of the third means being determined by supplying the gas at selectable inhalation stages of the breathing cycles of the user, and further comprising selector means for selectively setting the control means in either one of the two modes of operation supplying the gas by the second means and the third means, and means for overriding the selector means for setting the mode of operation supplying the gas by the first means.

11. A combination flow regulator and conservation device according to claim 10, and further comprising a removable cover portion, the removable cover portion enclosing the selector means to make it less accessible to changes in setting by the user.

12. A combination flow regulator and conservation device for supplying oxygen gas or oxygen concentrated gas to a user during the breathing cycles of the user, the device comprising means for regulating flow of the gas through the device, means for attaching the device to a tank containing or an outlet of a system supplying the oxygen or oxygen concentrated gas, and means for controlling both an effective rate and timing of the flow of gas through the device to selectively supply the gas to the user in one of at least three selectable modes of operation, the modes of operation including (a) first means for supplying a continuous flow of gas through at least the inhalation cycles of the user, (b) second means for providing an intermittent pulse of gas supplied to the user on at least the initial stage of inhalation of substantially every breathing cycle of the user, the second means including means for supplying the pulse of gas at selectively different periods of time during the initial stage of inhalation, and (c) third means for supplying an intermittent pulse of gas to the user at selectively different effective rates of flow of the gas, the pulse supplied by the third means being of a fixed time period for at least two of the selective effective rates, and the effective rates of the third means being determined by supplying the gas at selectable inhalation stages of the breathing cycles of the user, wherein the means for controlling both the effective rate and the timing of the flow of gas further comprises valve means for discharging the gas when moved from a closed position to an open position, and means responsive to an inhalation by the user for actuating the valve means, the means actuating the valve means including first means for retaining the valve means in the open position and second means operable only at initiation of movement from the closed position for overcoming any initial inertia in the valve means.

13. A combination flow regulator and conservation device according to claim 12, wherein the valve means comprises a valve body defining a central axial bore in fluid connection with the supply of gas, and a peripheral bore in fluid connection with the connecting means to deliver the gas under pressure to the valve means, the central bore and the peripheral bore being in selective fluid connection with each other, a valve seat selectively closing the fluid connection between the central bore and the peripheral bore by moveable engagement with the central bore in the axial line of the central bore, the delivered gas applying a first force to bias the valve seat in a direction for sealed engagement with the central bore, spring means for applying a second force also to bias the valve seat in a direction for sealed engagement with the central bore, the combined first and second forces being sufficient to hold the valve seat in sealed position, and electrical power means for applying a counter force to overcome the combined forces to move the valve seat away from the sealed position to an open position, the power means required to maintain the valve seat in the open position requiring only an amount of power to provide a reduced counter force sufficient to overcome the second force.

14. A combination flow regulator and conservation device according to claim 13, wherein the electrical power means comprises first means for providing substantially only that amount of the counter force needed to maintain the valve seat in the open position and second means operable only at initiation of movement for providing the balance of the counter force which together with the first providing means is substantially only needed for overcoming any initial inertia in moving the valve seat from the sealed position.

* * * * *